(12) United States Patent
Alberth et al.

(10) Patent No.: US 10,932,728 B2
(45) Date of Patent: *Mar. 2, 2021

(54) METHOD AND SYSTEM FOR IDENTIFYING LOCATION OF A TOUCHED BODY PART

(71) Applicant: Google Technology Holdings LLC, Mountain View, CA (US)

(72) Inventors: William P. Alberth, Prairie Grove, IL (US); Rachid M. Alameh, Crystal Lake, IL (US); Timothy Dickinson, Crystal Lake, IL (US)

(73) Assignee: Google Technology Holdings LLC, Mountain View, CA (US)

( * ) Notice: Subject to any disclaimer, the term of this patent is extended or adjusted under 35 U.S.C. 154(b) by 446 days.

This patent is subject to a terminal disclaimer.

(21) Appl. No.: 15/897,793

(22) Filed: Feb. 15, 2018

(65) Prior Publication Data

US 2018/0168520 A1 Jun. 21, 2018

Related U.S. Application Data

(63) Continuation of application No. 13/249,382, filed on Sep. 30, 2011, now Pat. No. 9,924,907.

(51) Int. Cl.
*A61B 5/00* (2006.01)
*A61B 34/00* (2016.01)
(Continued)

(52) U.S. Cl.
CPC ............ *A61B 5/7435* (2013.01); *A61B 5/748* (2013.01); *A61B 5/1114* (2013.01); *A61B 5/4824* (2013.01);
(Continued)

(58) Field of Classification Search
CPC ..... A61B 5/7435; A61B 5/748; A61B 5/4824; A61B 34/25; A61B 5/1114; A61B 2560/0295; G06F 3/0346
See application file for complete search history.

(56) References Cited

U.S. PATENT DOCUMENTS 5,515,858 A 5/1996 Myllymaki
5,788,657 A 8/1998 Burns
(Continued)

FOREIGN PATENT DOCUMENTS

EP 1615187 1/2006
GB 2409278 6/2005
JP 2012098987 5/2012

OTHER PUBLICATIONS

"Final Office Action", U.S. Appl. No. 13/249,382, dated May 12, 2015, 22 pages.
(Continued)

*Primary Examiner* — Sean P Dougherty
(74) *Attorney, Agent, or Firm* — Colby Nipper

(57) ABSTRACT

A method and system for identifying location of a touched body part. The method includes initializing a tracking system for monitoring travel of a pointer useful for indicating a touching operation, wherein the touching operation is performed on a body part. In addition, the method includes monitoring the travel of the pointer from a predetermined first location to a second location, wherein the second location coincides with a touch endpoint on a body part; and identifying the location of body part that was touched by the pointer.

21 Claims, 4 Drawing Sheets

(51) Int. Cl.
*A61B 5/11* (2006.01)
*G06F 3/0346* (2013.01)

(52) U.S. Cl.
CPC ....... *A61B 34/25* (2016.02); *A61B 2560/0295* (2013.01); *G06F 3/0346* (2013.01)

(56) References Cited

U.S. PATENT DOCUMENTS

| | | | |
|---|---|---|---|
| 5,797,854 | A | 8/1998 | Hedgecock |
| 5,803,915 | A | 9/1998 | Kremenchugsky et al. |
| 5,902,968 | A | 5/1999 | Sato et al. |
| 6,147,678 | A | 11/2000 | Kumar et al. |
| 6,204,852 | B1 | 3/2001 | Kumar et al. |
| 6,226,548 | B1 | 5/2001 | Foley et al. |
| 6,475,153 | B1 | 11/2002 | Khair et al. |
| 7,173,604 | B2 | 2/2007 | Marvit et al. |
| 7,292,151 | B2 | 11/2007 | Ferguson et al. |
| 7,374,536 | B1 | 5/2008 | Taylor |
| 7,667,657 | B2 | 2/2010 | Koshiji |
| 8,773,352 | B1 | 7/2014 | Huang |
| 9,052,710 | B1 | 6/2015 | Farwell |
| 9,924,907 | B2 * | 3/2018 | Alberth ............... A61B 5/7435 |
| 2001/0032059 | A1 | 10/2001 | Kelly et al. |
| 2002/0036618 | A1 | 3/2002 | Wakai et al. |
| 2003/0121766 | A1 | 7/2003 | Chen et al. |
| 2003/0139652 | A1 | 7/2003 | Kang et al. |
| 2003/0233053 | A1 | 12/2003 | Woolf et al. |
| 2004/0063501 | A1 | 4/2004 | Shimokawa et al. |
| 2004/0128012 | A1 | 7/2004 | Lin |
| 2005/0212759 | A1 | 9/2005 | Marvit et al. |
| 2005/0212760 | A1 | 9/2005 | Marvit et al. |
| 2005/0212767 | A1 | 9/2005 | Marvit et al. |
| 2007/0021845 | A1 | 1/2007 | Schweizer et al. |
| 2007/0032229 | A1 | 2/2007 | Jones |
| 2007/0265075 | A1 | 11/2007 | Zalewski |
| 2007/0270220 | A1 | 11/2007 | Kaneshige et al. |
| 2007/0273504 | A1 | 11/2007 | Tran |
| 2007/0288263 | A1 | 12/2007 | Rodgers |
| 2008/0015017 | A1 | 1/2008 | Ashida et al. |
| 2008/0036737 | A1 | 2/2008 | Hernandez-Rebollar |
| 2008/0051639 | A1 | 2/2008 | Iliff |
| 2008/0107303 | A1 | 5/2008 | Kim et al. |
| 2008/0139907 | A1 | 6/2008 | Rao et al. |
| 2008/0294058 | A1 | 11/2008 | Shklarski |
| 2009/0003673 | A1 | 1/2009 | Haimerl et al. |
| 2009/0036799 | A1 | 2/2009 | Sandhu et al. |
| 2009/0054067 | A1 | 2/2009 | Gauthier et al. |
| 2009/0054077 | A1 | 2/2009 | Gauthier et al. |
| 2009/0054751 | A1 | 2/2009 | Babashan et al. |
| 2009/0163787 | A1 | 6/2009 | Mannheimer et al. |
| 2009/0207246 | A1 | 8/2009 | Inami et al. |
| 2009/0226071 | A1 | 9/2009 | Schuler et al. |
| 2009/0296991 | A1 | 12/2009 | Anzola |
| 2010/0195867 | A1 | 8/2010 | Kipman et al. |
| 2010/0195869 | A1 | 8/2010 | Geiss |
| 2010/0235794 | A1 | 9/2010 | Ording |
| 2010/0249529 | A1 | 9/2010 | Sun et al. |
| 2010/0259475 | A1 | 10/2010 | Huang et al. |
| 2010/0312188 | A1 | 12/2010 | Robertson et al. |
| 2011/0105955 | A1 | 5/2011 | Yudovsky et al. |
| 2011/0109329 | A1 | 5/2011 | Diebold et al. |
| 2011/0118752 | A1 | 5/2011 | Itkowitz et al. |
| 2011/0118753 | A1 | 5/2011 | Itkowitz et al. |
| 2012/0013529 | A1 | 1/2012 | McGibney et al. |
| 2012/0050154 | A1 | 3/2012 | Jagmag |
| 2012/0071891 | A1 | 3/2012 | Itkowitz et al. |
| 2012/0071892 | A1 | 3/2012 | Itkowitz et al. |
| 2012/0075111 | A1 | 3/2012 | Ranta |
| 2012/0113001 | A1 | 5/2012 | Yamauchi et al. |
| 2012/0165615 | A1 * | 6/2012 | Choi ............... G16H 40/67 600/300 |
| 2012/0218183 | A1 | 8/2012 | Givon et al. |
| 2013/0053661 | A1 | 2/2013 | Alberth et al. |
| 2013/0085410 | A1 | 4/2013 | Alberth et al. |
| 2013/0253834 | A1 | 9/2013 | Slusar |
| 2013/0265437 | A1 | 10/2013 | Thörn et al. |
| 2013/0338548 | A1 | 12/2013 | Nakamura |
| 2014/0253429 | A1 | 9/2014 | Dai et al. |
| 2015/0234572 | A1 | 8/2015 | Arita et al. |

OTHER PUBLICATIONS

"Final Office Action", U.S. Appl. No. 13/222,293, dated Jan. 5, 2016, 19 pages.

"Non-Final Office Action", U.S. Appl. No. 13/249,382, dated Dec. 8, 2014, 21 pages.

"Non-Final Office Action", U.S. Appl. No. 13/222,293, dated Apr. 20, 2015, 12 pages.

"Non-Final Office Action", U.S. Appl. No. 13/249,382, dated Mar. 21, 2016, 12 pages.

"Non-Final Office Action", U.S. Appl. No. 13/249,382, dated Apr. 5, 2016, 10 pages.

"Non-Final Office Action", U.S. Appl. No. 13/249,382, dated Apr. 3, 2017, 10 pages.

"Notice of Allowance", U.S. Appl. No. 13/249,382, dated Nov. 15, 2017, 8 pages.

"Restriction Requirement", U.S. Appl. No. 13/249,382, dated Sep. 2, 2014, 10 pages.

"Restriction Requirement", U.S. Appl. No. 13/222,293, dated Oct. 2, 2014, 7 pages.

"Restriction Requirement", U.S. Appl. No. 13/249,382, dated Nov. 2, 2016, 6 pages.

* cited by examiner

METHOD AND SYSTEM FOR IDENTIFYING LOCATION OF A TOUCHED BODY PART

PRIORITY PARAGRAPH

This application is a divisional of and claims priority to U.S. patent application Ser. No. 13/249,382 filed Sep. 30, 2011 entitled "Method and System for Identifying Location of a Touched Body Part", the disclosure of which is incorporated by reference herein in its entirety.

FIELD OF THE DISCLOSURE

The present disclosure relates generally to identifying a body part that may be ailing. More specifically, the disclosure relates to tracking movement of a pointer as the pointer travels to an ailing body part.

BACKGROUND

For ages medical personnel have inquired of a person that is ill or injured, "Where does it hurt?" Modem technology can now provide a picture of a body for identifying a body part where an ailment occurs. For example, an image of a body or body type may be displayed on a smartphone's display screen. In this particular case, the displayed image has to be touched by an individual. Specifically, an image of a human body is displayed; thereafter, a user identifies a specific body part on the image that the user believes contains his ailment. This approach requires several advanced steps by a user, for example, launching an image for display, identifying the location of the body part in the image that the user wants to identify, and then correctly identifying the ailing body part. In addition, an inherent amount of image processing that requires large amounts of data and data analyzing is subject to a system of this kind.

Accordingly, there is a need for a method and system for identification of touch to a body part.

BRIEF DESCRIPTION OF THE FIGURES

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

Figure 1:
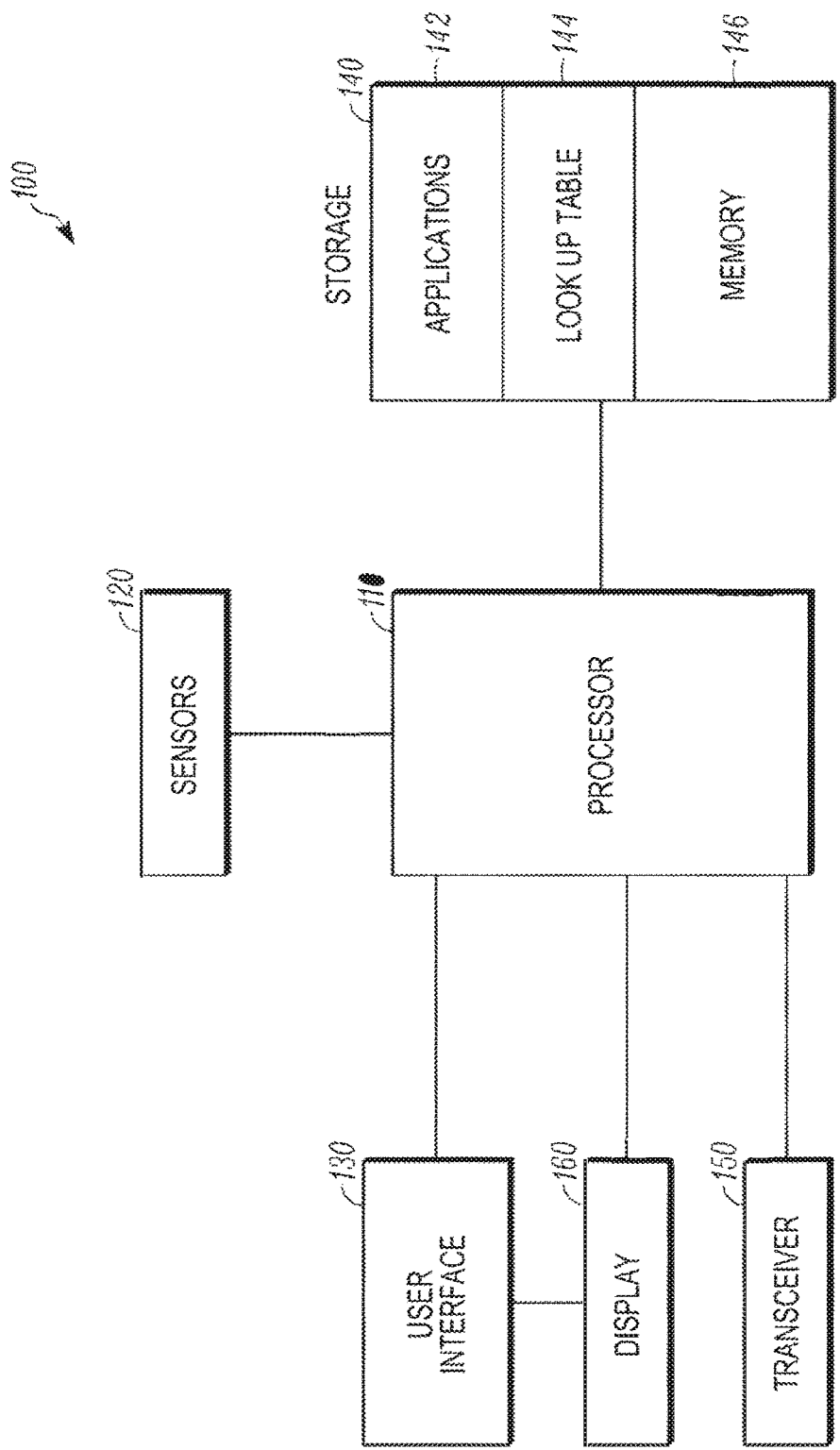
FIG. 1 is a block diagram of a networked system in accordance with some embodiments.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION

Described herein is a method for identifying location of a touched body part. The method includes initializing a tracking system for monitoring travel of a pointer useful for indicating a touching operation, wherein the touching operation is performed on a body part. In addition, the method includes monitoring the travel of the pointer from a predetermined first location to a second location, wherein the second location coincides with a touch endpoint on a body part; and identifying the location of body part that was touched by the pointer.

FIG. 1 is a block diagram of a networked system 100 that can be implemented internally in a wearable device. System 100 includes several components for operability. The described components are not an exhaustive list and are not intended to be limited to those described herein. Instead, the described components provide enlightenment by way of example of communicatively coupled components that are useful and capable of accomplishing the method described herein. Along these lines, a processor 110 is shown that may have a dual core processor, or a quad-core processor, or greater to perform algorithmic operations, data collection and analysis, for example. Processor 110 represents processing power and thus may be multiple processors communicatively coupled or networked together. The networked computers can exist in a cloud-type environment involving several servers. Processor 110 may also be referred herein as a controller that manages the network and electrical signals used by system 100.

Processor 110 in FIG. 1 receives electrical input signals from one or more sensors 120. Sensors 120 monitor the external or ambient conditions of a wearable device and the user's interaction with the wearable device. Several different types of sensors may be employed to monitor location, audio, speed, environment, device operational mode, proximity of the wearable device to the user, and activity of the wearable device user. These sensors can include a camera, a proximity sensor, a microphone, an accelerometer, a gyroscope, a galvanic skin response sensor, a temperature sensor, a visible light sensor, a touch sensor, a contact sensor, a wireless sensor, a pressure sensor, and ultrasonic sensor, an altitude sensor, and gesture detection sensors.

Processor 110 is also communicatively coupled to a user interface 130 that can be deployed on the wearable device. User interface 130 provides an input interface for the user of the wearable device to interact with the processor 110 and provide data to the processor 110. For example user interface 130 may be a touchscreen capable of input from a finger or a stylus. The touchscreen may be resistive or capacitive and may include electrophoretic components. User interface 130 may be a keyboard as well; and can be qwerty-type or can include another layout like T-9, for example. Alternatively, user interface 130 may employ both a keyboard and a touchscreen.

User interface 130 works cooperatively with display 160 and processor 110. Display 160 can be either an LED, LCD, AMOLED, or inorganic LED display, for example. Display 160 provides resolution, brightness and contrast capabilities to the wearable device.

Processor 110 also is communicatively coupled or networked to a storage device 140. Storage device 140 can be internal or remote from the wearable device or may be temporarily connected as in the case of a USB flashdrive, for example. Storage device 140, as shown, includes an application storage sector 142, a lookup table or database sector 144, and a cache memory sector 146. All or part of memory or storage functions can be remote or alternatively onboard.

Applications storage sector 142 works cooperatively with the user interface 130 through the processor 110 via a communication network. Applications storage sector 142 can store applications that may have been downloaded by the user or that may have been already installed on the wearable device by the manufacturer or other third party entity. The applications can enable a user of the wearable device to assess their location, their date and time, and their contact information in addition to their current wellness condition.

To assess current wellness conditions, a lookup table 144 or database can be employed to store known wellness conditions that may include ailments, injuries, rashes, user history profile, medical profile, or other medical assessments that would normally be found in a medical dictionary or online medical website. A cache memory 146 enables quick retrieval of the stored information that has either been input by the user or that has been requested by the user.

System 100 also employs a transceiver 150 that enables transmission and reception of communication signals such as WiFi, Bluetooth, and cellular signals, including 4G LTE and 3G.

Figure 2:
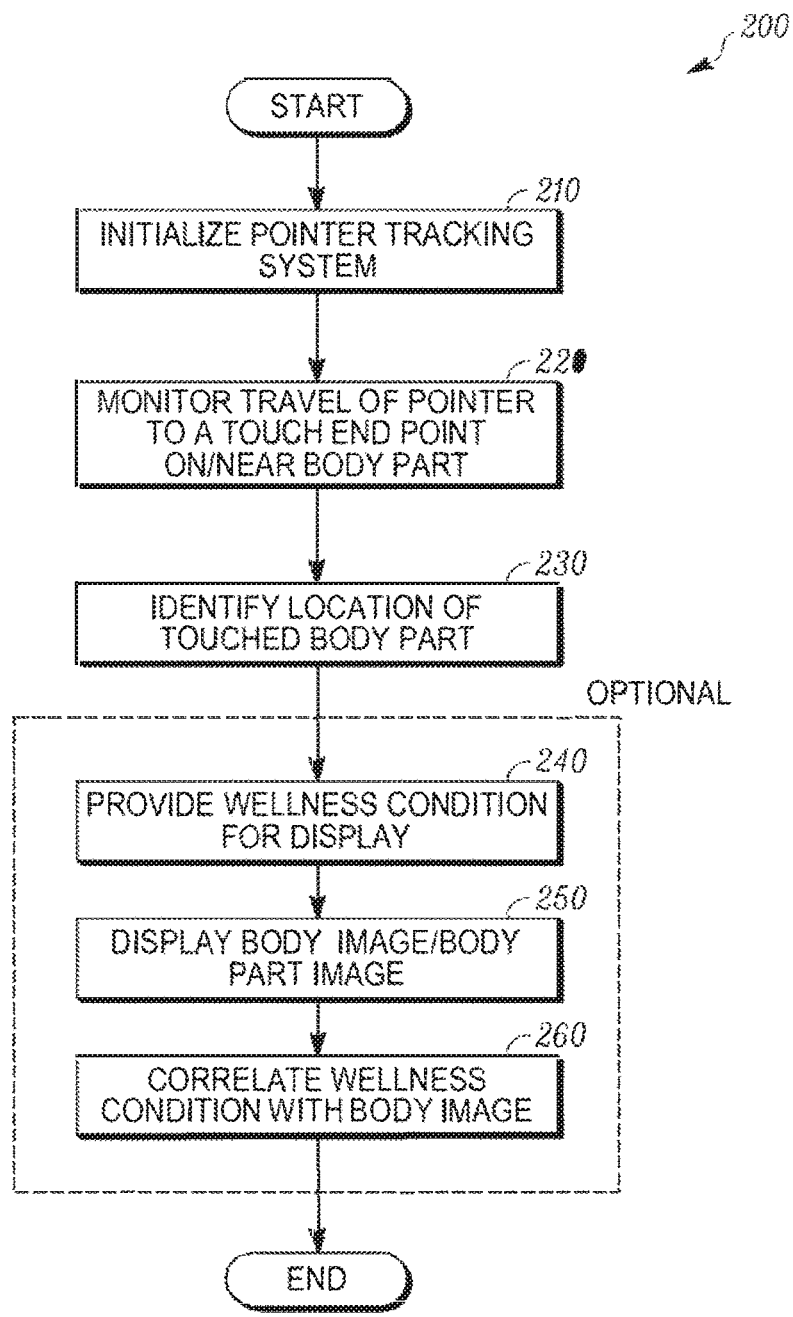
FIG. 2 is a flowchart of a method of identifying location of a touched body part in accordance with some embodiments.

FIG. 2 is a flowchart of a method 200 of identifying location of a touched body part. Upon starting or launching the instruction set or application, operation 210, of method 200, initializes a pointer tracking system. The pointer tracking system may employ a gyroscope, an accelerometer, or positioning software for tracking a pointer's movement or gesture making ability. The pointer can be a hand, an arm, a finger, a foot, a toe, a nose, a tongue, a head, or a mechanical pointing device, or other means of indicating or communicating an ailment or wellness condition. For example, an armless individual may learn to wink a number of times to communicate. A CCD or CMOS sensor or imager can be employed to count the number of winks or blinks of the armless user of the wearable device. The pointer can also be wielded by the user of the wearable device or another person.

Specifically, operation 220 in one embodiment monitors travel of pointer to a touch endpoint on or near a body part. The monitoring operation may involve tracking the location, rotation, acceleration, deceleration, tilts, pitch, yaw, sudden speed changes, orientation, and speed of the pointer as it moves from a starting point to an endpoint. The pointer may be voice implemented and its movement voice-controlled as well.

Operation 230 identifies location of touched part after the pointer has reached its endpoint. End point is detected by one or a combination of above sensors. Operation 230 may incorporate an imager or microphone or other sensor for identifying specific body part. This could be a multi-step process. First step is to identify a general area such as the chest region, then user interface guides user to zoom in and touch a specific chest location, e.g., the heart region after confirming initial chest selection.

Optionally, one or more additional operations may be implemented in method 200. For example, operation 240 may provide wellness conditions for display upon the wearable device. These wellness conditions enable a user of the wearable device to be able to select a particular wellness condition, such as an ailment, by touching the display of the wearable device or speak the ailment type to the device such as "heart" which is inputted following voice recognition operation.

Operation 250 displays an entire body image or body part image. Subsequent to the display of the wellness condition and the selection by the user of one or more wellness conditions, a body image appears on the display for the aiding the user in selecting the location of the appropriate part of the body where the wellness condition is most relevant. The body image may appear on the display as the user holds his pointer on his wellness condition. As such, the displayed image of the wellness conditions fades and the body image appears.

Operation 260 correlates wellness condition with body image. This operation enables a user to drag and drop a selected wellness condition upon the displayed body image. Operation 260 may also highlight the touched body part on the displayed body image. Additionally, operation 260 updates the system's memory with the selected body part and wellness condition as well as additional information such as identification, encryption, location, date, and time, for example.

Additional optional operations may enable notification of the selected body part to be transmitted or displayed upon the wearable device.

Figure 3:
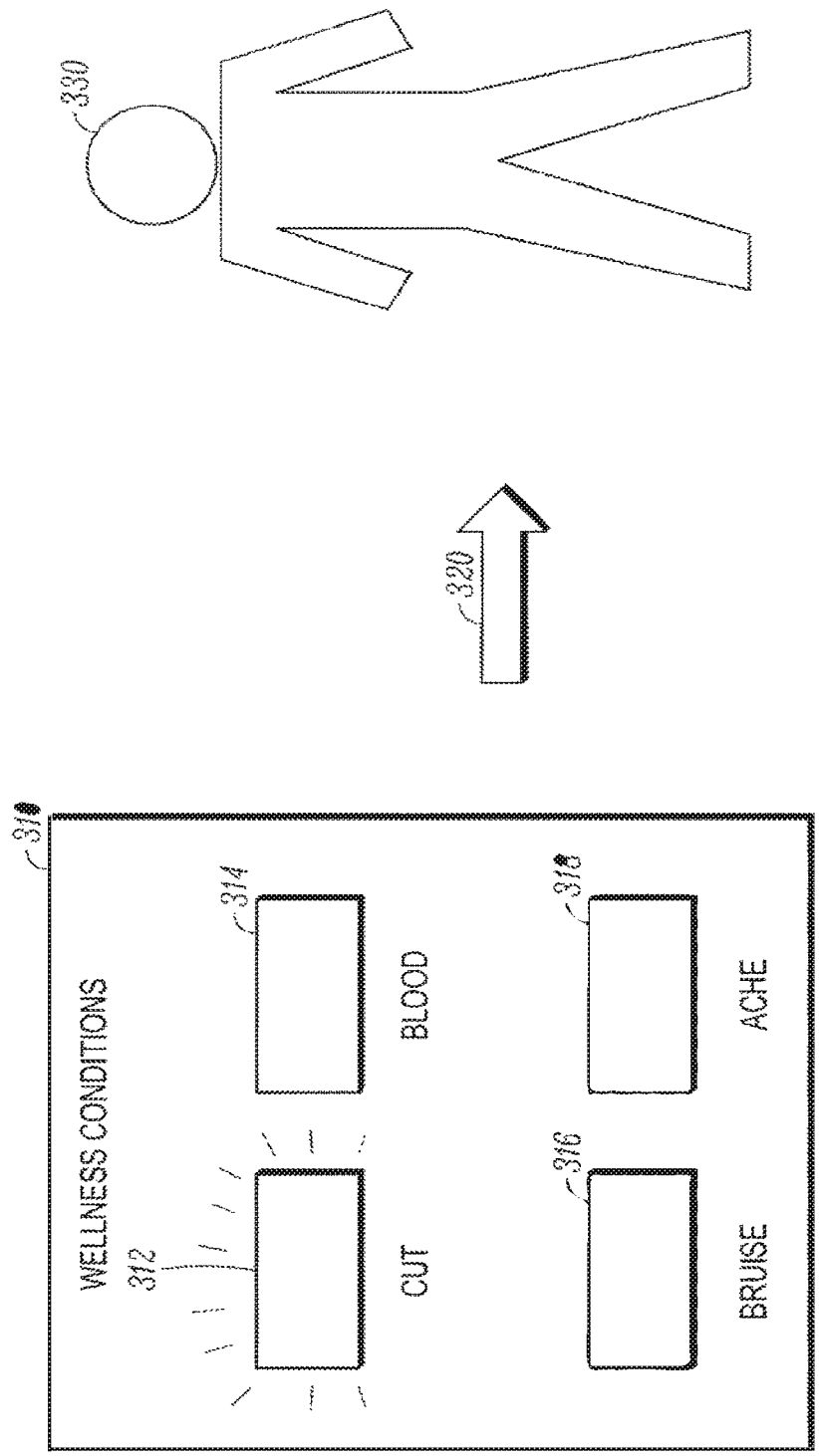
FIG. 3 is an exemplary illustration of a dynamically changing user interface in accordance with some embodiments.

FIG. 3 is an exemplary illustration of a dynamically changing user interface as initially described above. Image 310 is provided on the wearable device as a user interface for selecting wellness conditions. The number of wellness conditions is many and are limited by the size of the display and pre-filtering according to regions of a body, for example. Specifically, a migraine assessment may not be offered for selection of a leg injury because of pre-filtering of wellness condition. Accordingly, wellness conditions 312 (cut), 314 (blood), 316 (bruise), and 318 (ache) can be selected by the user to best describe the user's current condition. A user of the wearable device may employ voice input or touch or gesture movement to identify a wellness condition or select wellness condition from a display screen that includes wellness conditions, such as ailments, that may be associated with one or more identified body locations by using pre-filtering schemes or algorithms. The pre-filtering enables a list of wellness conditions to fit a limited screen size for the wearable device. Pressing or saying wellness condition 312 (a cut) highlights the selection.

Holding the selection allows the displayed image to dynamically transform or morph into a body image 330. Body image 330 can be gender based or animal based. Body image 330 includes several locations where the selected wellness condition 312 may apply. A user drags and drops 320 the selected wellness condition 312 to a specific location or body part upon body image 330. Alternatively, in cooperation with pre-filtering one or more individual body parts may be displayed rather than an entire body image. The user may be given notification, either written or audible or both, to indicate and verify the selected body part is what they had intended.

Specifically, a user performs a single continuous action for identifying wellness conditions. The user interface displays a wellness condition screen including one or more icons representative of various ailments, for example, (cut, pain, numbness, etc). User touches an individual icon and the user interface switches screen content from ailment types to an image of a body while the user is still touching the icon. Subsequently, the user drags the ailment icon to a specific body location on the newly appeared body image. That single continuous movement for a user's finger (touch, drag, lift off the icon) identifies the ailment type, its location, and updates memory with this new input condition automatically.

Figure 4:
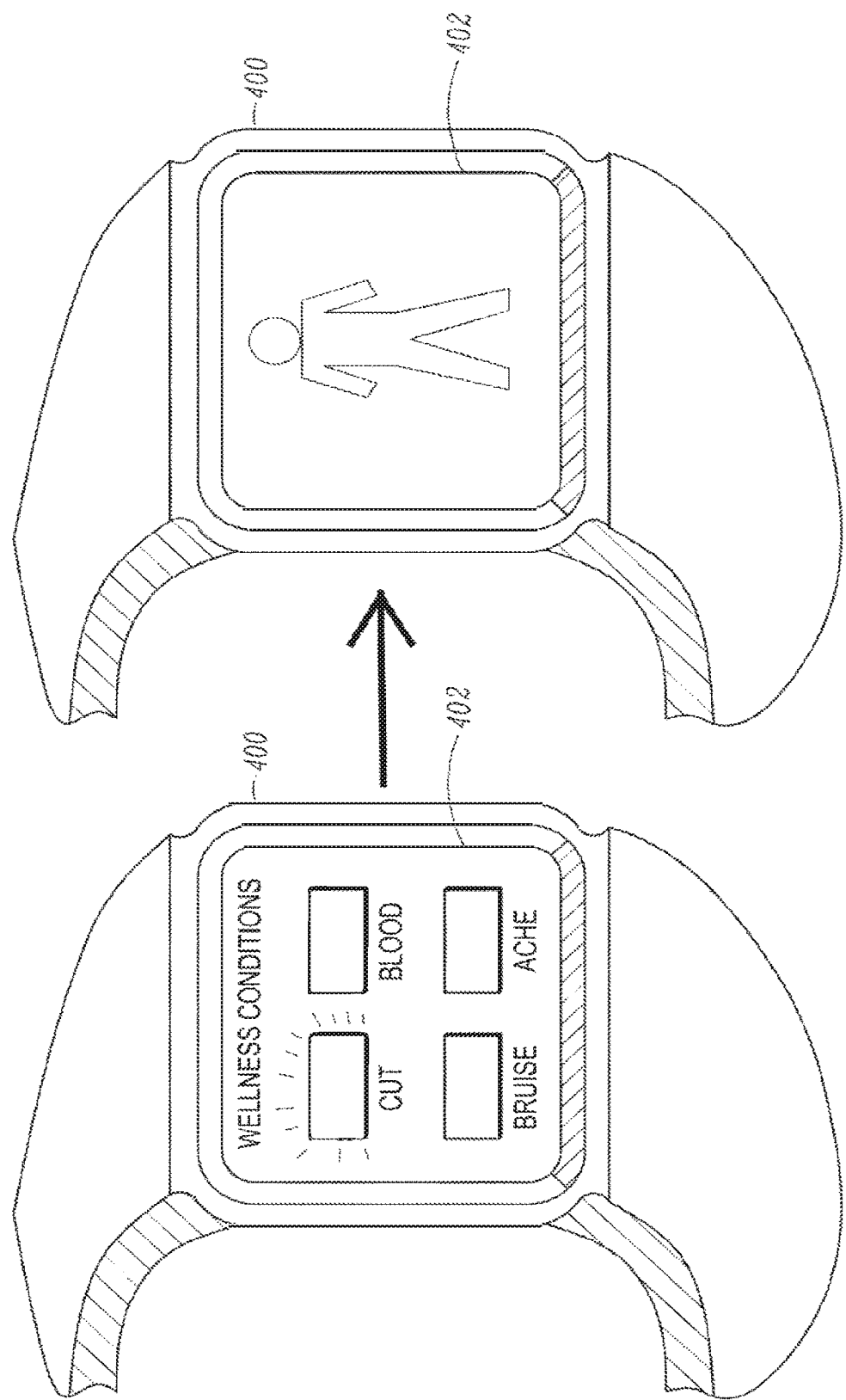
FIG. 4 is an exemplary illustration of the dynamically changing user interface of FIG. 3 on a wearable device.

FIG. 4 is an exemplary illustration of the dynamically changing user interface of FIG. 3 on the wearable device. Wearable device 400 includes a display screen 402 that incorporates a user interface. By way of example, the device may be a wrist worn electronic device, but need not be so always. The user manipulates the user interface to activate the health application. The application may request the user to "show me where it hurts". The user moves his hand with the wrist worn device to his chest. Sensors in the device (camera, gyroscope, accelerometer, etc) and track the motion of the hand and detect where the user is touching. By tracking the movement, the user interface can determine which part of the body the user intends to indicate.

In one instance, the user interface of the wearable device is a display of wellness conditions. In another instance, the user interface of the wearable device is a display of a body image. The user interface of the wearable device may dynamically change from one user interface displaying one or more images to another user interface that displays a different set of images.

Advantageously, there is no need for several screens to be consecutively displayed; and a single action gesture may be used to identify a wellness condition and location of an associated body part relevant to the wellness condition.

More than one wellness condition may exist for a user. For example, a user may experience an ache in their jaw at one moment in time and numbness in one arm later in time. The user then can select both conditions and have them stored for later derivation.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A wrist-wearable computing device comprising:
a processor, the processor located within the wrist-wearable computing device and configured to cause the wrist-wearable computing device to:
identify, using a tracking system that is located within the wrist-wearable computing device, a location on a body of a user wearing the wrist-wearable computing device, the location being touched by the user corresponding to a general area on the body of the user;
determine, based on the processor executing a pre-filtering algorithm using the identified location, wellness conditions associated with the general area on the body of the user;
present, using a display screen that is located within the wrist-wearable computing device, wellness condition images associated with the determined wellness conditions;
receive, from the user, a selection of one of the wellness condition images, the selection an indication of a particular wellness condition; and
transform, based on the selection and using the display screen, the presentation of the wellness condition images to another presentation of body parts near the general area.

2. The wrist-wearable computing device as described in claim 1, wherein the tracking system includes any combination of a camera, a proximity sensor, an accelerometer, a gyroscope, a temperature sensor, a visible light sensor, a touch sensor, a contact sensor, a wireless sensor, a pressure sensor, an ultrasonic sensor, an altitude sensor, or a gesture detection sensor.

3. The wrist-wearable computing device as described in claim 1, wherein the processor is further configured to cause the wrist-wearable computing device to monitor external or ambient conditions including a location, an audible sound, a speed of the user, an environmental condition, a device operational mode, a proximity of the wrist-wearable computing device to the user, or an activity of the user.

4. The wrist-wearable computing device as described in claim 1, wherein the processor is further configured to cause the wrist-wearable computing device to identify the location of the touched body part using an imager or microphone that is within the wrist-wearable computing device.

5. The wrist-wearable computing device as described in claim 1, wherein the processor is further configured to determine the wellness conditions based on a region of the body.

6. The wrist-wearable computing device as described in claim 1, wherein the wrist-wearable computing device is configured to receive the selection of the at least one wellness condition image through the display screen receiving a touch from the user or through a microphone that is within the wrist-wearable computing device and receiving audio from the user.

7. The wrist-wearable computing device as described in claim 1, wherein the display screen is a Light Emitting Diode (LED) Display, a Liquid Crystal Display (LCD), an Active-Matrix Organic Light-Emitting Diode (AMOLED) Display, or an inorganic LED display.

8. A wrist-wearable computing device comprising:
a processor, the processor located within the wrist-wearable computing device and configured to cause the wrist-wearable computing device to:
identify, using a tracking system that is located within the wrist-wearable computing device, a location of a touched body part on a body of a user wearing the wrist-wearable computing device;
determine, based on the processor executing a pre-filtering algorithm using the identified location, wellness conditions;
present, using a display screen that is located within the wrist-wearable computing device, wellness condition images associated with the determined wellness conditions;
receive, from the user, a selection of one of the wellness condition images;
correlate, based on a drag and drop operation performed by the user on the display screen, a body part to the selected wellness condition; and
update, using the processor, a memory device that is located within the wrist-wearable computing device information that indicates the correlated body part and the selected wellness condition associated to the selected wellness condition image.

9. The wrist-wearable computing device as described in claim 8, wherein the tracking system includes any combination of a camera, a proximity sensor, an accelerometer, a gyroscope, a temperature sensor, a visible light sensor, a touch sensor, a contact sensor, a wireless sensor, a pressure sensor, an ultrasonic sensor, an altitude sensor, or a gesture detection sensor.

10. The wrist-wearable computing device as described in claim 8, wherein the processor is further configured to cause the wrist-wearable computing device to monitor external or ambient conditions including a location, an audible sound, a speed of the user, an environmental condition, a device operational mode, a proximity of the wrist-wearable computing device to the user, or an activity of the user.

11. The wrist-wearable computing device as described in claim 8, wherein the processor is further configured to cause the wrist-wearable computing device to identify the location of the touched body part using an imager or microphone that is within the wrist-wearable computing device.

12. The wrist-wearable computing device as described in claim 8, wherein the processor is further configured to determine the wellness conditions based on a region of the body.

13. The wrist-wearable computing device as described in claim 8, wherein the wrist-wearable computing device is configured to receive the selection of the wellness condition image through the display screen receiving a touch from the user or through a microphone that is within the wrist-wearable computing device and receiving audio from the user.

14. The wrist-wearable computing device as described in claim 8, wherein the display screen is a Light Emitting Diode (LED) Display, a Liquid Crystal Display (LCD), an Active-Matrix Organic Light-Emitting Diode (AMOLED) Display, or an inorganic LED display.

15. The wrist-wearable computing device as described in claim 8, wherein the processor is further configured to direct the wrist-wearable computing device to transmit a notification of the selected body part that is correlated to the selected wellness condition.

16. A wrist-wearable computing device comprising:

a computer-readable storage medium that is located within the wrist-wearable computing device, the computer-readable storage medium storing a health application that, upon execution by a processor that is located within the wrist-wearable computing device, directs the wrist-wearable computing device to:

request, through a user interface that is located within the wrist-wearable computing device, a user wearing the wrist-wearable computing device to touch a location on a body of the user;

identify, using a tracking system that is located within the wrist-wearable computing device, one or more body parts near the touched location;

determine, based on the processor executing a pre-filtering algorithm using the touched location, wellness conditions associated with the one or more body parts;

present, using a display screen that is located within the wrist-wearable computing device, wellness condition images associated with the determined wellness conditions;

receive, from the user, a selection of one of the wellness condition images;

transform, based on the selection and using the display screen, the presentation of the wellness condition images to another presentation of the one or more body parts; and receive, from the user, a selection of one of the one or more body parts, the selection correlating the selected wellness condition to the selected body part.

17. The wrist-wearable computing device as recited in claim 16, wherein the health application, upon execution by a processor, further directs the wrist-wearable computing device to present a body image on the display of the device, the body image associated with the location.

18. The wrist-wearable computing device as recited in claim 16, wherein user interface includes the display screen.

19. The wrist-wearable computing device of claim 16, wherein the computer-readable storage medium includes a flash memory.

20. The wrist-wearable computing device of claim 19, wherein the computer-readable storage medium is in an application storage sector of the flash memory.

21. The wrist-wearable computing device of claim 20, wherein the health application, upon execution by a processor, further directs the wrist-wearable computing device to request, through the user interface, the user to input a location of the user, a date and time, or contact information of the user.

* * * * *